United States Patent [19]
Luebke et al.

[11] Patent Number: 5,283,373
[45] Date of Patent: Feb. 1, 1994

[54] ETHERIFICATION WITH SKELETAL OLEFIN ISOMERIZATION

[75] Inventors: Charles P. Luebke, Mount Prospect; Bipin V. Vora, Darien; David A. Wegerer, Lisle; Joseph E. Zimmermann, Arlington Heights, all of Ill.

[73] Assignee: UOP, Des Plaines, Ill.

[21] Appl. No.: 997,461

[22] Filed: Dec. 28, 1992

Related U.S. Application Data

[63] Continuation-in-part of Ser. No. 883,636, May 15, 1992, Pat. No. 5,210,327.

[51] Int. Cl.$^5$ .......................... C07C 41/06; C07C 5/22
[52] U.S. Cl. .................................... 568/697; 585/310; 585/314
[58] Field of Search .................. 568/697; 585/310, 314

[56] References Cited

U.S. PATENT DOCUMENTS

| | | | |
|---|---|---|---|
| 3,634,535 | 1/1972 | Haunschild | 260/677 A |
| 4,270,929 | 6/1981 | Dang Vu et al. | 44/56 |
| 4,282,389 | 8/1981 | Droste et al. | 568/697 |
| 4,330,679 | 5/1982 | Koehler et al. | 568/697 |
| 4,361,422 | 11/1982 | Derrien et al. | 44/56 |
| 4,513,153 | 4/1985 | Sandrin | 568/697 |
| 4,554,386 | 11/1985 | Groeneveld et al. | 568/697 |
| 4,581,474 | 4/1986 | Hutson Jr. et al. | 568/697 |
| 4,778,943 | 10/1988 | Sun | 585/671 |
| 4,814,517 | 3/1989 | Trubac | 568/697 |
| 4,814,519 | 3/1989 | Harandi et al. | 568/697 |
| 4,950,803 | 8/1990 | Smith Jr. et al. | 568/697 |
| 5,008,455 | 4/1991 | Schleppinghoff | 568/697 |

*Primary Examiner*—Howard T. Mars
*Attorney, Agent, or Firm*—Thomas K. McBride; John G. Tolomei

[57] ABSTRACT

A combination of an etherification process and a process for the isomerization of linear alkenes to isoalkenes uses a separation zone that receives an effluent stream from the etherification reaction zone and separates it into a high boiling stream, a low boiling stream and an intermediate boiling stream in order to reduce the mass flow of reactants through the isomerization and etherification reaction zones. The separation zone includes at least one distillation column. The distillation column can provide a distillation function only, or can also provide a reactive distillation zone. The intermediate boiling stream leaves a two column separation zone as a bottoms stream from a second column or in a single column separation zone as a sidecut which in the case of reactive distillation is taken from the point above a bed of catalyst within the column. Taking the sidecut stream substantially eliminates the circulation of isoalkane hydrocarbons through the etherification and isomerization zone and maintains normal alkanes at an acceptable equilibrium level. The effluent from the isomerization zone may enter the first in a series of etherification zones or may enter a second etherification zone having higher capacity.

19 Claims, 1 Drawing Sheet

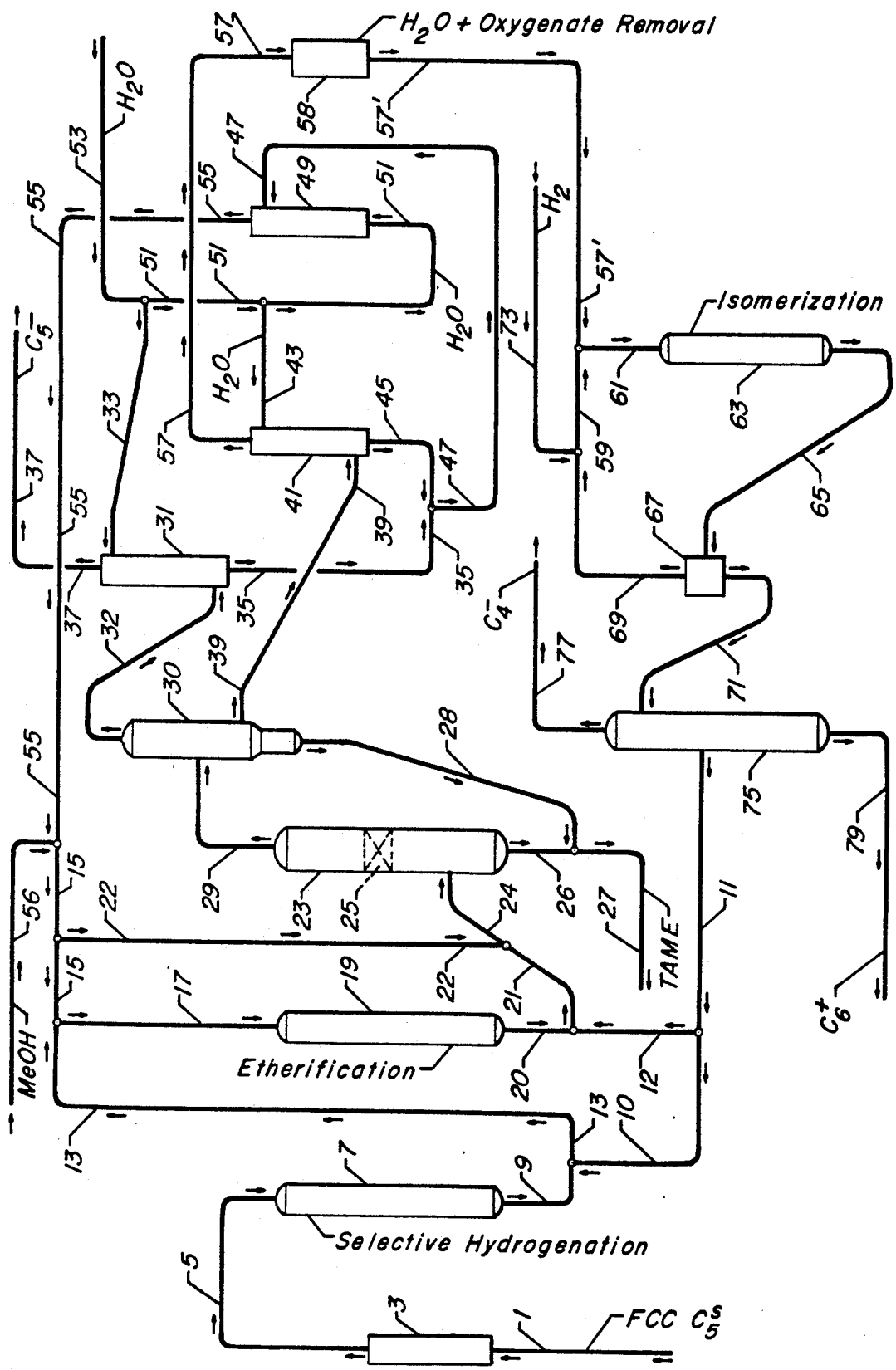

ETHERIFICATION WITH SKELETAL OLEFIN ISOMERIZATION

CROSS-REFERENCE TO RELATED APPLICATION

This application is a continuation in part of Ser. No. 883,636 filed on May 15, 1992 now U.S. Pat. No. 5,210,327.

FIELD OF THE INVENTION

This invention relates to processes for the production of ethers by the reaction of an alcohol with an isoolefin. More specifically this invention relates to a process for the production of ether and the skeletal isomerization of olefins to provide additional feedstock for the production of ethers.

BACKGROUND OF THE INVENTION

The production of ethers by the reaction of an isoolefin and an alcohol are well known commercial operations. There are many detailed descriptions of processes for the production of such ethers, in particular, methyl tertiary butyl ether (MTBE) and methyl tertiary amyl ether (TAME). These ethers have long been known as useful octane blending agents for gasoline motor fuels due to their high octane number (RON) of about 120. More recently ether compounds as gasoline blending components have been highly valued as supplying oxygen to meet reformulated gasoline requirements. Processes for the production of MTBE and TAME by reacting methanol with isobutylene or isoamylene, respectfully, are among the most widely known processes for the production of such ethers.

Processes for the production of such ethers have suffered from a shortage of the necessary isoolefins for reaction with the alcohols to provide products. Feedstreams for etherification processes typically consist of a wide variety of olefinic and paraffinic isomers. It has been known to increase the available feedstock by the dehydrogenation of paraffins and the skeletal isomerization of olefins. Methods for the dehydrogenation of paraffins, in particular isoparaffins, are well known in the art as are processes for the skeletal isomerization of normal olefins to isoolefins. Since the olefinic and paraffinic isomers of any given carbon number have relatively close boiling points, separation of the isomers in an efficient manner to enhance the production of ether as well as the conversion of unreacted products to additional reactants have been difficult. Methods for the various separations have included adsorptive separations as well as extractive distillations. There is a need for etherification and isomerization process arrangements that simplify the separation of olefinic and paraffinic isomers to provide products and reactants. There is also a need to have processes for that can incorporate the additional reactants from skeletal isomerization zones into existing etherification facilities.

SUMMARY OF THE INVENTION

This invention is a process that combines an etherification zone with a skeletal olefin isomerization zone in an arrangement that separates the higher boiling ether products from the lower boiling alcohols and isoparaffins while leaving an intermediate boiling stream that supplies linear alkenes to skeletal olefin isomerization zone. The removal of the intermediate boiling stream concentrates a feedstream of linear alkenes to the reaction zone for the skeletal isomerization of the normal alkenes to isoalkenes. By taking the feedstream as an intermediate boiling cut, isoparaffins are rejected and linear alkenes are recycled while maintaining a low mass flow through the isomerization zone. Rejection of the isoparaffins from the feedstream eliminates the need for a drag stream of paraffins that was often required to prevent the build-up of such unreacted hydrocarbons in the recycle loop of the combined process. The overall smaller flowrate to the isomerization zone lowers the overall capital and operating cost of the unit while adding only additional minor cost to the distillation system for the combined process. The intermediate stream may be withdrawn as a sidecut from a reactive distillation zone or as a bottoms stream from a second column. At least a portion of the additional isoalkene reactants from the isomerization zone enter a second etherification zone to reduce the mass flow through a first etherification zone which is often an existing reaction zone.

In one embodiment this invention is a process for the production of ether from a feedstream including normal alkene, isoalkene, normal alkane and isoalkane isomers. The process includes the steps of mixing an etherification input stream comprising isoalkenes, normal alkenes and normal alkanes with a $C_1$–$C_5$ monohydroxy alcohol to produce a first combined feed and contacting the first combined feed with an etherification catalyst in a first etherification zone at etherification conditions to react isoalkenes with the alcohol and produce a first etherification effluent stream comprising ether and normal alkane and normal alkene isomers. At least a portion of the first etherification zone effluent and at least a portion of an isomerization zone effluent stream produce a second combined etherification feed that contacts an etherification catalyst at etherification conditions in a second etherification zone to produce a second etherification zone effluent comprising ether, normal alkane, normal alkene and isoalkane isomers and separating at least a portion of the second etherification zone effluent in a distillation zone into a high boiling fraction comprising ether, a low boiling fraction comprising isoalkane, and an intermediate boiling fraction having an average boiling point between the low boiling and the high boiling fraction the intermediate fraction comprising normal alkene and normal alkane isomers of the isoalkane. At least a portion of the intermediate boiling stream passes as an isomerization zone feed to an isomerization reaction zone for the skeletal isomerization of normal alkenes and contacts an isomerization catalyst at isomerization conditions. The process withdraws an isomerization zone effluent stream comprising isoalkenes from the isomerization zone and passes at least a portion of the isomerization zone effluent to the second etherification zone to provide at least a portion of the second combined etherification zone feedstream. At least a portion of the feedstream including normal alkene, isoalkene, normal alkane and isoalkane isomers passes into the etherification zone.

Additional aspects of this invention relate to the arrangements required for distillation of feedstreams, reaction zone locations and treatment zones. In particular, another aspect of this invention is the reaction of unsaturated $C_4$ hydrocarbon isomers to produce MTBE and the reaction of unsaturated $C_5$ isomers for the production of methyl tertiary amyl ether. Another aspect of this invention is to withdraw the intermediate boiling stream as a sidecut from a distillation zone. The distillation zone may also provide reactive distillation to enhance the conversion of product feed streams and the recovery of potential reactants.

BRIEF DESCRIPTION OF THE DRAWING

The FIGURE shows a schematic illustration of a process of this invention showing the etherification zone, isomerization zone, distillation zone along with additional separators, and treating zones for the purification of the feedstream and product.

DETAILED DESCRIPTION OF THE INVENTION

This invention is broadly applicable to the production of a wide variety of ethers from a number of different feedstocks. The primary ethers for which this invention will be applied are tertiary, amyl and butyl ethers. The advantages of this invention are achieved when the feedstream includes a mixture of normal and branched alkene and alkane isomers. Where the etherification process is one for the production of butyl ethers, the typical feedstream will consist of a mixture of $C_4$ isomers comprising isobutane, isobutene, normal butane, 1-butene and 2-butene. Where the process is one for the production of amyl ethers, the feedstream components will include 3,methyl-1-butene, isopentane, 1-pentene, 2,methyl-1-butene, normal pentane, trans-2-pentene, cis-2-pentene and 2,methyl-2-butene in a typical distribution of isomers. Since in the combination of etherification and skeletal olefin isomerization processes, the alkanes are not reacted to any significant degree, these components increase the amount of material that passes through the process and must be removed to prevent an unacceptable build-up of unreacted products that circulate through the process. Although a variety of sources are available to provide such feedstreams, the most common source of the feedstreams for these processes are light cracked hydrocarbon streams from an FCC unit, or a $C_4$ stream from a stream cracker after butadiene extraction.

Often these hydrocarbon streams will contain diolefins in addition to the desired monoolefin feed components. These diolefins interfere with the operation of the catalyst in downstream processes by polymerizing and forming heavy hydrocarbon compounds that block the active sites of the catalyst and prevent their use. Preferably, feedstreams for this process will undergo treatment for the elimination of diolefins. A common method of eliminating diolefins is by the selective hydrogenation of the diolefins to saturate the diolefins into monoolefins while preserving monoolefins. Those skilled in the art know a variety of selective hydrogenation processes for the saturation of diolefins to monoolefins. A particular catalyst and operating conditions for such selective hydrogenation processes can be found in U.S. Pat. Nos. 4,695,560 and 4,734,540 the contents of which are hereby incorporated by reference. The selective hydrogenation process typically employs a nickel on aluminum catalyst or a noble metal, such as palladium on alumina, for the selective hydrogenation. The nickel may be sulfided or unsulfided. The process can also operate at a broad range of operating conditions including pressures of from 40 to 800 psig with pressures of between 50 and 300 psig being preferred and temperatures of from 70°-700° F. with temperatures of from about 120°-400° F. being preferred. Effective space velocities for the processes should be above 1 hr$^{-1}$ and preferably are above 5 with a range of from between 5 to 35 hrs$^{-1}$. It is typical in such processes to limit the amount of hydrogen to prevent the saturation of monoolefins such that there is less than 2 times the stoichiometric amount of hydrogen required for the selective hydrogenation in the process. Preferably, the mol ratio of hydrogen to diolefinic hydrocarbons in the material will be in a range of from 1:1 to 1.8:1, and in some cases the hydrogen will be less than stoichiometrically required amount of hydrogen. Additional information related to the selective hydrogenation of diolefinic hydrocarbons, and in particular, unconjugated diolefinic hydrocarbons, can be found in U.S. Pat. No. 4,695,560.

The feed to the process includes an alcohol to react with the isolefin and produce the desired ether product. The alcohols that can be used are typically $C_1$-$C_5$ monohydroxy alcohols. Methanol typically constitutes the alcohol of choice for the etherification process. Ethanol, although used less commonly, is also a commonly available alcohol for the etherification process. Methanol is preferred somewhat since it is a stable commercial chemical of long standing.

The isoalkene as well as the normal alkene hydrocarbons will enter an etherification zone along with the alcohol. Contact with the etherification catalyst at etherification conditions will produce the ether product. A wide range of materials are known to be effective as etherification catalysts for the isoalkene reactants including mineral acids such as sulfuric acid, boron trifluoride, phosphoric acid on kieselguhr, phosphorus-modified zeolites, heteropoly acids, and various sulfonated resins. The use of a sulfonated solid resin catalyst is preferred. These resin type catalysts include the reaction products of phenolformaldehyde resins and sulfuric acid and sulfonated polystyrene resins including those crosslinked with divinylbenzene. A particularly preferred etherification catalyst is a macroporous acid form sulfonic ion exchange resin such as a sulfonated styrene-divinylbenzene resin as described in U.S. Pat. No. 2,922,822 having a degree of crosslinking of from about 5 to 60%. Suitable resins are available commercially. Specialized resins have been described in the art and include copolymers of sulfonyl fluorovinyl ether and fluorocarbons as described in U.S. Pat. No. 3,849,243. Another specially prepared resin consists of the $SiO_2$-modified cation exchangers described in U.S. Pat. No. 4,751,343. The macroporous structure of a suitable resin is described in detail in U.S. Pat. No. 5,012,031 as having a surface area of at least 400 m$^2$/g, a pore volume of 0.6-2.5 ml/g and a mean pore diameter of 40-1000 angstroms. It is contemplated that the subject process could be performed using a metal-containing resin which contains one or more metals from sub-groups VI, VII or VIII of the Periodic Table such as chromium, tungsten, palladium, nickel, chromium, platinum, or iron as described in U.S. Pat. No. 4,330,679. Further information on suitable etherification catalysts may be obtained by reference to U.S. Pat. Nos. 2,480,940, 2,922,822, and 4,270,929 and the previously cited etherification references.

A wide range of operating conditions are employed in processes for producing ethers from olefins and alcohols. Many of these include vapor, liquid or mixed phase operations. Processes operating with vapor or mixed phase conditions may be suitably employed in this invention. The preferred etherification process uses liquid phase conditions.

The range of etherification conditions for processes operating in liquid phase still includes a broad range of suitable conditions including a superatmospheric pressure sufficient to maintain the reactants as a liquid phase, generally below about 700 psig, and a temperature between about 85° and about 210° F. Even in the presence of additional light materials, pressures in the range of 140 to 580 psig are sufficient. A preferred temperature range is from 100°-210° F. The reaction rate is normally faster at higher temperatures but conversion is more complete at lower temperatures due to favorable thermodynamic equilibrium. High conversion in a moderate volume reaction zone can, therefore, be obtained if the initial section of the reaction zone, e.g., the first two-thirds, is maintained above 160° F. and the remainder of the reaction zone is maintained below 120° F. This may be accomplished most easily with two reactors. The ratio of feed alcohol to isoolefin should normally be maintained in the broad range of 1:1 to 2:1. With the isobutene and isopentene reactants, good results are achieved if the ratio of methanol to isobutene is between 1.05:1 and 1.5:1. An excess of methanol, above that required to achieve satisfactory conversion at good selectivity, should be avoided as some decomposition of methanol to dimethyl ether may occur which may increase the load on separation facilities. Various etherification process techniques, reaction conditions and product recovery methods are described in U.S. Pat. Nos. 4,219,678 to Obenaus et al. and 4,282,389 to Droste et al. which are incorporated herein for this teachings.

In this invention the etherification reactants pass through at least two etherification reaction zones. The first etherification reaction zone will typically receive only a portion of the additional reactants created by the isomerization of normal alkenes. Sending only a portion of the reactants through the first reaction zone maintains a lower mass flow through the first zone relative to the second etherification reaction zone. Reduced mass flow allows existing etherification reactor facilities to be utilized. In a preferred form all of the reactants produced by the isomerization of hydrocarbons in the isomerization zone will pass directly to the second to the etherification zone after any desired recovery of hydrogen and separation of light ends. Addition of alcohol to feed to the second etherification zone maintains the proper alcohol to isoolefin ratios.

The etherification zones operate selectively to principally convert only the isoolefins. Therefore, alkanes and normal alkenes pass through the etherification zone without any significant conversion to products or by-products. Thus, the etherification zone effluents together with the unreacted feed components provide a stream of ether product and normal and branched alkenes and alkane isomers for separation. In most cases, the stream entering the separation zone will also contain unreacted alcohol. The separation zone receiving the ether products, alcohol and unreacted hydrocarbons distills the product into three separate boiling point fractions. Similar to most separation systems for recovery of ethers, the product separation zone provides a high boiling fraction that principally contains ether product. The product separation zone of this invention separates the remaining lower boiling components into a low boiling fraction containing isoalkane and lower boiling components and an intermediate boiling fraction that contains normal alkenes and alkanes that were not reacted in the etherification process or enter the separation zone directly as part of the process feed. Isoparaffins typically provide the lowest boiling constituent of the alkene and alkane isomers. The isoalkane isomers are conveniently withdrawn with the low boiling fraction from the separation zone.

In a continuously circulating process of this invention, the normal alkanes must also find a path out of the process loop in order to prevent their build-up. Typically, this process arrangement will withdraw a portion of the normal alkanes with the low boiling fraction from the separation zone. Withdrawal of the normal alkanes with the low boiling fraction establishes an equilibrium concentration of normal alkanes that controls their build-up in the recycle loop of the invention. The cut point for the intermediate boiling stream is set to maximize the removal of the isoalkane hydrocarbons and minimize the loss of normal alkenes between the low boiling fraction and the intermediate fraction. The arrangement of the separation zone can consist of a single distillation column with the low boiling point fraction taken as an overhead, the high boiling point fraction taken as a bottoms stream, and the intermediate boiling point fraction taken as a sidecut from the column or a multiple column separation zone where the high boiling fraction is typically taken as an bottom stream and an overhead fraction undergoes subsequent separation in a separate column into the high boiling and intermediate boiling streams. Removal of the sidecut stream presents little problem for a typical etherification arrangement that already uses a distillation column. The sidecut of the normal alkene rich stream is taken a few trays below the overhead and will normally require the addition of only a few trays to the distillation column. It has been found that only a minimal amount of the normal alkene hydrocarbons are lost with the overhead by the method of this invention while still maintaining the equilibrium of normal alkanes circulating through the process at a reasonable level. The cut point between the high boiling fraction and the intermediate fraction is readily determined on the basis of maximizing the ether recovery. The separation between the low boiling fraction and the intermediate fraction is usually not critical when the ether is used for fuel blending purposes since the normal alkene and alkane hydrocarbons present in the intermediate stream are usually suitable gasoline components.

The separation zone of this invention is best suited to the production of a single ether product. For example, in the case of MTBE or TAME, the invention extracts one group of normal alkanes as the isomers for withdrawal from the separation zone as the intermediate boiling product. In the case of a typical MTBE process, the high boiling fraction will comprise MTBE, the low boiling fraction will include methanol and isobutane, and the composition of the intermediate fraction includes primarily normal butane, 1-butene and 2-butene. Intermediate stream withdrawal is set to minimize the loss of 1-butene with the overhead while taking out sufficient normal butane with the overhead to maintain a reasonable level of normal butane in circulation through the process. Where the process is used for the production of TAME, the high boiling stream comprises the ether product, isopentane and lesser amounts of normal pentane comprise major components of the low boiling stream, and the intermediate boiling fraction contains the normal pentene and some isopentene isomers along with a substantial quantity of normal pentane that is maintained at a desired concentration level through the circulating $C_5$ hydrocarbons. In the pentene operation, the separation point between the low boiling and high boiling streams again seeks to maximize isopentane recovery while minimizing the loss of normal pentenes.

A useful arrangement for the separation zone of this invention is the use of a reactive distillation zone that contains a bed of etherification catalyst. The distillation zone can thus provide the second etherification zone for etherification of reactants from the isomerization zone and additional etherification of unreacted isoalkanes from the first etherification zone to lower their concentration in the intermediate boiling sidecut stream. Therefore, the reactive distillation zone can be used as a combined reaction and separation zone with the removal of the intermediate boiling fraction from the combined reaction and distillation zone. Processes for the production of ether by catalytic distillation are well known to those skilled in the art and are taught in U.S. Pat. Nos. 3,634,535 and 4,950,803. Where the distillation zone is a catalytic distillation zone, the preferred arrangement introduces the feed to a point below a bed of catalyst within the distillation zone. The high boiling fraction is withdrawn from the higher boiling point region below the bed of catalyst while a lower boiling fraction can be withdrawn for further separation into the low boiling and intermediate boiling stream. In another embodiment the intermediate boiling stream is withdrawn as a sidecut from a single distillation zone and typically has a withdrawal point in the relatively lower boiling region above the bed of catalyst. Catalytic distillation for the production of ethers typically employs the same operating conditions as those generally taught for etherification. No particular apparatus or arrangement is needed to retain the catalyst bed within the distillation zone and a variety of methods can be used to incorporate the bed or region of catalyst within the distillation zone. For example, catalyst may be retained between suitable packing materials or may be incorporated on to a distillation tray itself. A preferred method of retaining the catalyst is through the use of corrugated structural devices and is described in U.S. Pat. No. 5,073,236 which is hereby incorporated by reference.

In most cases, the process arrangement will also include methods for recovering the unreacted alcohol. Those skilled in the art are familiar with the various azeotropes formed by the ether products and alcohol and can provide suitable means for such separations and recoveries. As anticipated for most cases, methanol will be the usual alcohol and both the low boiling point fraction and the intermediate fraction will ordinarily undergo an alcohol recovery step. Water washing provides the usual means for recovering methanol in such arrangements.

Following etherification and separation, the intermediate boiling fraction undergoes skeletal isomerization of the normal alkenes to produce additional isoalkenes for the etherification process. In order to maintain this catalyst stability in the isomerization zone, the streams contacting the catalyst may require removal of polar contaminants such as sulfur, nitrogen or oxygen compounds. Thus, in addition to processing for the recovery of methanol, the intermediate boiling fraction may also require additional purification for the removal of compounds that can poison the catalyst or interfere with the skeletal isomerization process. Compounds that are usually most harmful to the isomerization catalyst include water, oxygenate compounds and nitrogen compounds. The water and oxygenate compounds suppress the isomerization catalyst activity. The nitrogen compounds also affect the isomerization catalyst activity and results in a reduced activity. These nitrogen compounds are also poison to acidic ion exchange resins used for the etherification and thus are also beneficially removed prior to the etherification. A variety of methods are known to remove such compounds which include water washing, adsorption and extraction processes. Oxygenate compounds and nitrogen compounds can be removed by typical adsorbents for the removal of these contaminants comprised zeolitic molecular sieves. Suitable types of zeolites are faujasites having pore sizes of about 10 angstroms. In particular, such zeolites include X, Y and L types as described in U.S. Pat. Nos. 3,216,789; 2,882,244 and 3,130,007. A particularly preferred type of zeolite is 13X. The use of type 13X sieves for the removal of oxygenate compounds such as dimethyl ethers from the effluent from an etherification process is described in U.S. Pat. No. 4,814,517, the contents of which are hereby incorporated by reference. Suitable operation of the isomerization zone will require the removal of water and oxygenate compounds to a level of less than 50 wppm, and preferably less than 5 wppm water equivalents. Common nitrogen and oxygenate compounds that have also been found in light cracked products from an FCC unit include acetone and acetonitrile. These compounds are preferably removed by water washing such feeds prior to introduction into the process.

The normal alkene-rich input stream after purification enters the isomerization zone. Methods for converting the normal alkene components to isoalkene components by isomerization are well known in the art. A process for converting linear alkenes to isomerized alkenes using a crystalline or silicate molecular sieve is taught in U.S. Pat. No. 4,503,282. Additional catalyst and methods for the skeletal isomerization of linear alkenes are described in U.S. Pat. Nos. 4,778,943 and 4,814,519. A preferred catalyst for the isomerization reaction zone of this invention is a non-zeolitic molecular sieve. Preferred forms of the non-zeolitic molecular sieve for this invention includes silicoaluminophosphates and a magnesium aluminophosphate. Suitable non-zeolitic catalysts such as the SAPO and MgGAPO are described in U.S. Pat. No. 4,440,871 and 4,758,419 which are hereby incorporated by reference. The catalyst for the isomerization zone typically lies in a fixed bed arrangement. In order to permit in-situ regeneration, the isomerization zone may include multiple reactors in a swing bed arrangement. Preferably, the reactants contact the catalyst in a vapor phase flow. Contacting a linear alkene feed with a catalyst in the presence of hydrogen in a molar ratio of from about 0.01 to 9, and preferably in a ratio of from 1 to 7, aids the process by suppressing the formation of carbon compounds on the catalyst. The isomerization process will typically operate over a broad range of conditions including temperatures of from 120°–1300° F. with temperatures in the range of 200°–1000° F. being preferred and temperatures in a range of 450 to 800 being particularly preferred. Pressures for the isomerization reaction will also vary over a wide range extending from atmospheric conditions to 700 psig and preferably are in a range of 50 to 350 psig. Space velocities can also vary over a wide range from 0.5 to 100 $hr^{-1}$ with a preferred range of 1–5 $hr^{-1}$. The expected per pass conversion of normal alkenes to isoalkenes in the isomerization zone will generally reach at least 40% of the total combined feed entering the reaction zone and will more typically exceed 50%.

The effluent stream from the isomerization zone containing isoalkenes normally undergoes separation for the recovery of light gases including hydrogen. Hydrogen recovered in the light gases from the isomerization zone is recycled to the inlet of the isomerization zone to provide any necessary hydrogen concentration. The effluent from the isomerization zone may also undergo additional separation to remove additional light ends or reject heavier by-product hydrocarbons. The presence of light ends or the isomerization zone effluent passes this light material on to the etherification zone as uncondensibles that, when rejected from the etherification separation system, drag methanol into downstream facilities thereby causing corrosion problems and methanol loss. Heavy materials such as $C_6^+$ hydrocarbons tend to foul or deactivate the etherification catalyst.

In the simplest arrangement of this invention, at least a portion of the effluent from the isomerization zone, after any separation, is admixed with the feed to the second etherification zone to provide additional isoalkene reactants. In a preferred form of this invention the entire stabilized or unstabilized or unstabilized effluent from the isomerization reaction zone directly enters the second etherification reaction zone. The return of the isomerization effluent to the second etherification reaction provides a loop incorporating components that are recycled through the process. The arrangement of this invention is particularly advantageous where the recycle loop circulates a high concentration of unreacted components. With the by-passing of the recycled feed components around the first etherification zone it is unnecessary to design both etherification reaction zones for the large mass flow of unreacted components. Preferably, the feedstream of mixed, branched, and normal alkenes and alkanes will enter the process at a point in the loop just ahead of the etherification reaction zone. However, this feedstream may be added at a number of different points, depending on its composition, within this loop. For example, it is also possible to add the feedstream at a point just ahead of the distillation column. In this way the total flow of reactants through the etherification zone is reduced by eliminating non-reactive isoalkane hydrocarbons. For the purposes of this invention it is most common to charge as much of the fresh feed as possible to the first etherification zone and pass any remaining feed to the second etherification reactor. Those skilled in the art are aware of the particular characteristics of the feedstream and the desired product streams that will dictate the most advantageous location for introducing the feedstream.

EXAMPLE

This invention is further described in the context of an example for the production of methyl tertiary amyl ether using a process or an arrangement as shown in the Figure. This example presents engineering calculations based on data from operating process units and laboratory test results. Relative flowing compositions for the major process streams of this Example are shown in Table 1 on a water-free basis. In this example, a feed comprising a $C_5$ cut from the product stream of a fluidized catalytic cracking unit enters the process through line 1 and passes through a water wash zone 3. Water wash zone 3 removes soluble nitrogen compounds and light oxygenates from the feed. Line 5 recovers the purified feed at a liquid flow of 7026 barrels per day and passes the feed to a selective hydrogenation reactor 7 for the removal trace diolefin compounds. Line 9 carries the treated FCC feed which is saturated with water to a level of about 400 wppm and on a water-free basis and has the relative flowing composition given in Table 1. Line 9 admixes the treated FCC feed with 4973 barrels per day of recycle stream split from a line 11 by a line 10 and having a relative composition given in Table 1. Methanol in an amount of 620 lb-mol/hr carried by line 15 mixes with the combined feed carried by line 15 to provide an etherification feedstream passed by line 17 into an etherification reactor 19. Etherification reactor 19 contacts the combined feed with a sulfonated solid resin catalyst at a temperature of about 170° and a pressure of about 88 psig. Catalyst in etherification reactor 19 is arranged as a solid bed. A line 20 carries the effluent from etherification reactor 19 into admixture with the contents of a line 12 that carries the remaining portion of the recycle stream of line 11. A line 22 mixes 128 lb-mol/hr of methanol effluent and recycle stream transported by line 21 to provide a second reaction zone feedstream carried by a line 24 into a reactive distillation column 23 having a second bed of sulfonated solid resin catalyst 25 located in an upper portion of the distillation column. Table 1 lists the relative composition of line 21. The contents of line 24 enters column 23 at an average temperature of about 170° F. and a pressure of 88 psig. A bottoms stream 26 carries the tertiary methyl amyl ether product from the column and combines with an optional stream 28 of additional recovered product to provide a product stream 27 having the relative composition given in Table 1. An overhead stream 29 carries unreacted methanol, normal pentane, normal pentene, isopentane, and lighter hydrocarbons from column 23. A portion of the overhead carried by line 29 is cooled, condensed and refluxed to the top of column 23 after separation of light gases in a condensing section (not shown). Line 29 carries the remainder of the effluent to a second distillation column 30. Column 30 separates the overhead from column 23 into an overhead stream 32 comprising isopentane and alcohol that passes to a water wash column 31. Recycled and fresh water, entering column 31 from a line 33, carries methanol downward through the column where a line 35 takes the methanol along with the water. A $C_5$ drag stream in the form of the overhead line 37 leaves the top of water zone 31 and has the relative composition given in Table 1. Column 30 optionally provides a recovery of additional TAME product via a line 28. Recovering additional TAME product from the bottom of column 30 allows column 23 to operate with a rough split that minimizes the requirements of the reactive distillation section. Column 30 also provides a sidecut stream which is taken from a lower portion of column 30 by a line 39. Line 39 transfers the sidecut stream to a water wash column 41 for the removal of methanol and other oxygenate streams from the sidecut. A line 43 charges water to the top of water wash column 41 which is collected by a line 45 and combined with the methanol and water from water wash column 31 into a stream 47. The two water wash zones may be replaced with one zone by separating alcohol from the overhead fraction 29 and passing the remainder of the overhead to column 30. The contents of stream 47 enter a methanol separation column 49 for the recovery of water from the methanol stream. Water recovered from column 49 passes through a line 51 to supply water for column 41 through line 43 and is combined with make-up water from a line 53 to provide the water stream 33 for column 31. A line 55 carries methanol from the top of column 49 and combines it with fresh methanol entering by a line 56 to provide the methanol for the etherification through line 15. Water washed hydrocarbons from methanol recovery column 41 pass overhead via line 57 and through a water and oxygenate removal zone 58 for the withdrawal of trace amounts of oxygenates such as dimethyl ether and water. Treatment of stream 57 in zone 58 lowers the concentration of water and water equivalent in line 57 to less than 30 wppm and yields a stream having the composition given in Table 1. The contents of line 57' are combined with a hydrogen recycle stream which is carried by line 59 to form a combined feed 61 that enters a reactor 63 for the skeletal isomerization of normal pentenes to isopentenes. Table 1 lists the composition of the hydrogen recycle stream carried by line 59. The combined feed enters the isomerization reaction zone at a temperature of about 120° F. and a pressure of about 290 psia. The combined feed contacts a silicoaluminophosphate catalyst of the SAPO-11 type within the reaction zone. Line 65 withdraws the product effluent from the isomerization reactor which passes through a liquid vapor separation zone 67. The liquid vapor separation zone recovers a hydrogen rich stream 69 which mixes with additional makeup hydrogen from line 73 to provide the hydrogen recycle stream 59. A line 71 transfers the heavier components from separator 67 to a distillation column 75. Column 75 fractionates light ends comprising $C_4^-$ materials overhead through a line 77 and drops $C_6^+$ components out of the process through a line 79. Line 11, having the composition previously described, in a table carries the isopentane rich stream from column 75 for combination with the FCC feed.

TABLE 1

| STREAM COMPOSITION - MOL % | | | | | | | |
|---|---|---|---|---|---|---|---|
| | Line 9 | Line 11 | Line 21 | Line 27 | Line 37 | Line 57 | Line 59 |
| $H_2$ | — | — | .57 | — | .04 | — | 91.51 |
| $C_1$-$C_4$ | 5.44 | — | 2.67 | .19 | 9.58 | .87 | .35 |
| 3M-1-butene | 1.68 | .55 | .88 | — | 2.25 | 1.03 | .06 |
| isopentane | 35.70 | 56.81 | 37.14 | .11 | 67.78 | 57.66 | 5.11 |
| 1-Pentene | 4.98 | .87 | 2.30 | .03 | 3.30 | 4.03 | .07 |
| 2M-1-Butene | 9.60 | 4.41 | .55 | .01 | .19 | .25 | .33 |
| Normal Pentane | 6.18 | 14.01 | 8.13 | 3.47 | 8.91 | 14.14 | 1.34 |
| Trans-2-Pentene | 9.23 | 4.07 | 5.27 | 1.68 | 3.93 | 10.38 | .26 |
| Cis-2-Pentene | 7.48 | 3.50 | 4.36 | 1.80 | 2.99 | 8.52 | .22 |
| 2M-2-Butene | 16.99 | 12.45 | 5.50 | .27 | 1.00 | 2.90 | .74 |
| $C_5$ Cyclic | 1.15 | .21 | .53 | 2.42 | .02 | .22 | |
| $C_6^+$ | 1.56 | .38 | .77 | 3.99 | | | |
| $H_2O$ wppm | 400 | 400 | 400 | 400 | 400 | 400 | 400 |
| Methanol | — | — | 20.08 | | | | |
| TAME | — | — | 11.23 | 86.03 | | | |

What is claimed is:

1. A process for the production of ether from a feedstream including normal alkene, isoalkene, normal alkane and isoalkane isomers, said process comprising:

(a) mixing an etherification input stream comprising isoalkenes, normal alkenes and normal alkanes with a $C_1$-$C_5$ monohydroxy alcohol to produce a first combined feed and contacting said first combined feed with an etherification catalyst in a first etherification zone at etherification conditions to react isoalkenes with said alcohol and produce a first etherification effluent stream comprising ether and normal alkane and normal alkene isomers;

(b) mixing said first etherification zone effluent and at least a portion of an isomerization zone effluent stream produce a second combined etherification feed and contacting said second combined etherification feed with an etherification catalyst at etherification conditions in a second etherification zone to produce a second etherification zone effluent comprising ether, normal alkane, normal alkene and isoalkane isomers and separating at least a portion of said second etherification zone effluent in a distillation zone into a high boiling fraction comprising said ether, a low boiling fraction comprising said isoalkane, and an intermediate boiling fraction having an average boiling point between said low boiling and said high boiling fraction, said intermediate fraction comprising normal alkene and normal alkane isomers of said isoalkane;

(c) passing an isomerization zone feedstream comprising at least a portion of said intermediate boiling stream to an isomerization reaction zone for the skeletal isomerization of normal alkenes and contacting said intermediate boiling stream with an isomerization catalyst at isomerization conditions;

(d) withdrawing an isomerization zone effluent stream comprising isoalkenes from said isomerization zone and passing at least a portion of said isomerization zone effluent directly to said second etherification zone to provide at least a portion of said second combined etherification zone feedstream; and, (e) passing at least a portion of said feedstream including normal alkene, isoalkene, normal alkane and isoalkane isomers into said first etherification zone.

2. The process of claim 1 wherein said distillation zone includes a least two columns and said intermediate stream is recovered as a bottoms stream from one of said columns.

3. The process of claim 1 wherein said isomers comprise $C_4$ or $C_5$ hydrocarbons and said alcohol comprises methanol or ethanol.

4. The process of claim 1 wherein said distillation zone contains a bed of etherification catalyst to provide said second etherification zone.

5. The process of claim 1 wherein said low boiling stream contains a greater amount of said isoalkane isomer than said intermediate stream.

6. The process of claim 1 wherein said isomerization zone effluent stream passes directly to said second etherification zone.

7. The process of claim 1 wherein alcohol is admixed with said second combined feedstream.

8. The process of claim 1 wherein said distillation zone contains two distillation columns, a first column provides said high boiling fraction as a bottoms stream and a second column provides said intermediate boiling stream as a bottoms stream and said low boiling fraction as an overhead stream.

9. The process of claim 1 wherein said distillation zone contains two distillation columns, a first column provides said high boiling fraction as a bottoms stream and a second column provides said low boiling fraction as an overhead stream, said intermediate boiling stream as a sidecut stream and additional high boiling product as a bottoms stream.

10. A process for the production of tertiary amyl ether from a feedstream including normal pentane, isopentane, normal pentene, and isopentene, said process comprising:

(a) mixing said feedstream and an isomerization zone effluent stream with a $C_1$-$C_5$ monohydroxy alcohol to produce a combined feed and contacting said combined feed with an etherification catalyst in an etherification zone at etherification conditions to react isopentenes with said alcohol and produce an intermediate etherification effluent stream comprising tertiary amyl ether, unreacted alcohol, normal pentane, normal pentene, isopentene and isopentane;

(b) passing said intermediate etherification effluent and a least a portion of an isomerization zone effluent stream comprising isopentene as an input stream to a reactive distillation zone containing a bed of etherification catalyst and contacting said input stream in said bed of catalyst at etherification conditions, withdrawing from said distillation zone at a location below said bed of catalyst a high boiling fraction comprising said tertiary amyl ether, and withdrawing from said distillation zone at a location above said bed of catalyst, an overhead fraction comprising isopentane, normal pentene and normal pentane and separating said overhead fraction into a low boiling stream comprising unreacted isopentane, and an intermediate boiling stream comprising normal pentene and normal pentane, said intermediate boiling stream having a lower concentration of isopentane than said low boiling stream;

(c) passing said intermediate boiling stream to a reaction zone for the skeletal isomerization of normal pentenes and contacting said intermediate boiling stream with an isomerization catalyst at isomerization conditions; and, (d) withdrawing said isomerization zone effluent stream comprising isopentene from said isomerization zone and passing at least a portion of said isomerization zone effluent stream to said relative distillation zone.

11. The process of claim 11 wherein said alcohol comprises methanol and said product comprises a methyl tertiary amyl ether.

12. The process of claim 11 wherein said feedstream is contacted with a selective hydrogenation catalyst at selective hydrogenation conditions in a selective hydrogenation zone to selectively saturate diolefins to monoolefins.

13. The process of claim 11 wherein said intermediate boiling stream is mixed with a hydrogen rich recycle stream before entering said isomerization zone and the concentration of water, and oxygenate compounds in said intermediate boiling fraction is reduced to below 100 wppm of water equivalents before mixing said intermediate boiling stream with said hydrogen rich recycle stream.

14. The process of claim 11 wherein said isomerization effluent stream passes directly to said reactive distillation zone.

15. A process for the production of tertiary butyl ether from a feedstream including normal butene, isobutene, normal butane, and isobutane, said process comprising:

(a) mixing said feedstream and isomerization effluent stream with a $C_1$-$C_5$ monohydroxy alcohol to produce a combined feed and contacting said combined feed with an etherification catalyst in an etherification zone at etherification conditions to react isobutenes with said alcohol and produce an intemediate etherification effluent stream comprising tertiary butyl ether, unreacted alcohol, normal butane, normal butene, isobutane, and isobutene;

(b) passing said intermediate etherification effluent and at least a portion of an isomerization zone effluent stream comprising normal butene as an input stream to a reactive distillation zone containing a bed of etherification catalyst and contacting said input stream in said bed of catalyst at etherification conditions, withdrawing from said distillation zone at a location below said bed of catalyst a high boiling fraction comprising said tertiary butyl ether and withdrawing from said distillation zone at a location above said bed of catalyst an overhead fraction comprising isobutane, normal butene and normal butane and separating said overhead fraction into a low boiling stream comprising said isobutane and an intermediate boiling stream comprising normal butene and normal butane, said intermediate boiling stream having a lower concentration of isobutane than said low boiling fraction;

(c) passing said intermediate boiling stream to a reaction zone for the skeletal isomerization of normal butenes and contacting said intermediate boiling stream with an isomerization catalyst at isomerization conditions; and (d) withdrawing said isomerization zone effluent stream comprising isobutene from said isomerization zone and passing said isomerization zone effluent to said etherification reaction zone.

16. The process of claim 16 wherein said alcohol comprises methanol and said product comprises a methyl tertiary butyl ether.

17. The process of claim 16 wherein said feedstream is contacted with a selective hydrogenation catalyst at selective hydrogenation conditions in a selective hydrogenation zone to selectively saturate diolefins to monoolefins.

18. The process of claim 16 wherein said intermediate boiling stream is mixed with a hydrogen rich recycle stream before entering said isomerization zone and the concentration of water and oxygenate compounds in said intermediate boiling fraction are reduced to below 100 wppm of water equivalents before mixing said intermediate boiling with said hydrogen rich recycle stream.

19. The process of claim 16 wherein said isomerization effluent stream passes directly from said isomerization zone to said reactive distillation zone.

* * * * *